United States Patent [19]

Neumann et al.

[11] 4,307,253
[45] Dec. 22, 1981

[54] PROCESS FOR THE PREPARATION OF ALKYL ARYL ETHERS

[75] Inventors: Rainer Neumann; Hans-Helmut Schwarz, both of Krefeld; Dieter Nachtsheim, Dormagen, all of Fed. Rep. of Germany

[73] Assignee: Bayer Aktiengesellschaft, Leverkusen, Fed. Rep. of Germany

[21] Appl. No.: 110,034

[22] Filed: Jan. 7, 1980

[30] Foreign Application Priority Data

Jan. 26, 1979 [DE] Fed. Rep. of Germany ....... 2903020

[51] Int. Cl.$^3$ ............................................ C07C 41/00
[52] U.S. Cl. ................................... 568/630; 568/632; 568/648; 568/650; 568/651; 568/652; 568/656; 568/658
[58] Field of Search ............... 568/630, 652, 632, 656, 568/648, 650, 651, 658

[56] References Cited

U.S. PATENT DOCUMENTS

| | | | |
|---|---|---|---|
| 2,487,832 | 11/1949 | Searle | 568/630 |
| 2,781,404 | 2/1957 | Rosenwald | 568/650 |
| 2,782,239 | 2/1957 | Mavity | 568/650 |
| 3,584,058 | 6/1971 | Hahn | 568/630 |
| 4,153,810 | 5/1979 | Neumann et al. | 568/630 |

FOREIGN PATENT DOCUMENTS 251561  1/1967  Austria ............................... 568/630

*Primary Examiner*—Bernard Helfin
*Attorney, Agent, or Firm*—Sprung, Felfe, Horn, Lynch & Kramer

[57] ABSTRACT

Procecss for the preparation of alkyl aryl ethers by reacting phenols with aliphatic ethers in the presence of strongly acid cation exchangers.

6 Claims, No Drawings

PROCESS FOR THE PREPARATION OF ALKYL ARYL ETHERS

The invention relates to a process for the preparation of alkyl aryl ethers by reacting phenols with aliphatic ethers in the presence of strongly acid cation exchangers.

A large number of processes for the preparation of alkyl aryl ethers is known (see, for example, Houben-Weyl, Methoden der organischen Chemie (Methods of Organic Chemistry), Volume VI/3, page 54 et seq. (1965)). Thus, the etherification of phenols with aliphatic alcohols in the presence of acid cation exchangers (see Nippon Kaishi 8, 1513 (1974); U.S.S.R. Patent Specification No. 197,613; and DE-OS (German Published Specification) No. 2,655,826) and the etherification of phenols with aliphatic ethers in the presence of aqueous metal salt solutions (Austrian Patent Specification No. 251,561). However, these processes have considerable disadvantages. Thus, the process which uses aliphatic ethers as the alkylating agent suffers considerable corrosion, effluent and separation problems.

Of the processes which opeate with aliphatic alcohols as the alkylating agent in the presence of strongly acid cation exchangers, only the process described in DE-OS (German Published Specification) No. 2,655,826 gives good yields of alkyl aryl ethers. However, these yields are preferentially achieved with primary aliphatic alcohols. When secondary and tertiary alcohols are used, the yields of alkyl aryl ethers which are free from products alkylated in the nucleus decrease as a result of increasing alkylation in the nucleus.

It has now been found, surprisingly, that aryl alkyl ethers containing only a small proportion of compounds which are alkylated in the nucleus can be prepared on an industrial scale, in an economical manner and in good yields, by etherifying phenols with ethers of aliphatic alcohols in the presence of strongly acid cation exchangers.

The invention thus relates to a process for the preparation of aryl alkyl ethers by alkylating phenols in the presence of strongly acid cation exchangers, which is characterised in that ethers of aliphatic alcohols are used as the alkylating agent.

The process according to the invention is particularly suitable for alkylating phenols to introduce secondary and tertiary aliphatic alkyl radicals, above all for isopropylating phenols.

The molar ratio phenol:aliphatic ether is of no significance in the process according to the invention. Since the aliphatic ethers to be used as the alkylating agent are good solvents for the phenols to be etherified, the ethers are employed in an amount such that a homogeneous phenol solution is obtained at the reaction temperature.

Examples which may be mentioned of representatives of the phenols to be alkylated according to the invention are: phenol, phenols substituted by $C_1$-$C_4$-alkyl groups, such as m-, o- and p-cresol, xylenols and tert.-butylphenol, phenols substituted by halogen atoms, such as m-, o- and p-chlorophenol and 2,4-dichlorophenol, and furthermore polyphenols, such as pyrocatechol, resorcinol, hydroquinone and 1,2,4-trihydroxybenzene, and also $\alpha$- and $\beta$-naphthol and hydroxyanthracene.

The aliphatic ethers used as the alkylating agent in the process according to the invention are ethers, the aliphatic radicals of which contain 1 to 8, preferably 1 to 4, carbon atoms. Examples which may be mentioned are: dimethyl ether, diethyl ether, dipropyl ether, diisopropyl ether, diisobutyl ether and di-tert.-butyl ether.

Some of these aliphatic ethers are obtained as waste products in the preparation of the corresponding aliphatic alcohols. The process according to the invention enables these waste products to be utilised appropriately.

In principle, all the strongly acid cation exchangers based on synthetic resins can be used in the process according to the invention. Strongly acid cation exchangers of this type are described, for example, in Kirk-Othmer, Encyclopedia of Chemical Technology, 2nd Edition, Volume 11, pages 871 and et seq. The strongly acid cation exchangers can be either in the form of a gel or macroporous. The cation exchangers are employed in the process according to the invention in their $H^+$ form. The cation exchangers are preferably used in the form of commercially available bead polymers, but also in the form of granules or in powder form.

The amount of strongly acid cation exchanger can vary within wide limits in carrying out the process according to the invention. In general, the strongly acid cation exchanger is employed in amounts of 0.5 to 50% by weight, preferably 1 to 25% by weight, relative to the weight of the starting compounds.

Since the aliphatic ethers to be used as the alkylating agent are good solvents for the phenols to be etherified, use of a solvent can in general be dispensed with.

The process according to the invention can be carried out under reduced pressure, normal pressure or excess pressure. To achieve high reaction rates and good space/time yields, it can be advantageous to carry out the process under increased pressure. This applies, above all, when low-boiling aliphatic ethers which are gaseous at the reaction temperature are employed. In this case, pressures which are above the autogenous vapour pressure of the lowest-boiling component are appropriate.

The process according to the invention can be carried out, for example, by a procedure in which the phenol to be etherified is dissolved in the ether serving as the alkylating agent, the strongly acid cation exchanger is added to the solution and the mixture is warmed to reaction temperatures of 20° to 150° C., preferably 50° to 130° C.

The process according to the invention can be carried out discontinuously and continuously. The continuous procedure has proved particularly suitable. For example, the reaction mixture consisting of the phenol, aliphatic ether and catalyst can be reacted continuously in a reactor by introducing the mixture at one end of the reactor and, after a certain residence time at the desired reaction temperature, removing it continuously from the reactor. It has proved particularly advantageous to locate the catalyst in a fixed bed in the reactor. In this case, the phenol/ether mixture is passed through the acid cation exchanger, located in a fixed bed, in a continuous stream.

A particularly advantageous embodiment, which can be carried out discontinuously or continuously, of the process according to the invention, through which the formation of compounds which are alkylated in the nucleus is considerably reduced, that is to say the selectivity of the alkylation reaction is greatly increased, consists of a procedure in which, when the reaction had ended, the alkyl aryl ether and the compounds which have lower boiling points than the latter, such as water, alcohol and dialkyl ethers, are distilled off from the reaction mixture and the distillation residue is reacted again, if appropriate after completing the phenol and/or dialkyl ether consumed by the alkyl aryl ether formation.

The surprising aspect of this procedure is that the proportion of compounds which are alkylated in the nucleus decreases by re-using the distillation residue and does not remain the same, as was to be expected.

In this procedure, it can be advantageous to carry out the reaction only to a certain percentage of the theoretical conversion.

The reaction mixtures obtained in the process according to the invention are worked up by processes which are in themselves known: if the process has not been carried out in a fixed bed, the solid catalyst is first removed by customary methods of solid/liquid separation, such as filtering, centrifuging, sedimenting and decanting. The catalyst can be re-used for fresh reactions. Water formed during the reaction and unreacted aliphatic ether are first separated off from the liquid phase by distillation. The residue which remains contains the alkyl aryl ether formed, which is isolated by processes which are in themselves known, for example distillation or crystallisation.

The alkyl aryl ethers obtainable by the process according to the invention are intermediate products for the preparation of agents for combating pests, dyestuffs and auxiliary products for plastics (see DE-AS (German Published Specification) No. 1,643,358), odour substances, antioxidants and preservatives (see Ullmann's Enzyklopädie der technischen Chemie (Ullmann's Encyclopaedia of Industrial Chemistry), Volume 13, page 450 (1962)).

The parts indicated in the following examples are parts by weight, unless otherwise indicated.

EXAMPLE 1

282 parts of phenol and 56.4 parts (=20% by weight) of a dry, strongly acid cation exchanger (polystyrenesulphonic acid crosslinked with 4% by weight of divinylbenzene) are heated to 120° C. in a three-necked flask provided with a stirrer, reflux condenser, thermometer and gas inlet tube. 10 parts of dimethyl ether are then passed into the reaction mixture in the course of 2½ hours. As was determined by gas chromatography, the reaction mixture had the following composition: 251 parts of phenol, 35.6 parts of anisole, 3 parts of water and 2.5 parts of dimethyl ether. The proportion of products alkylated in the nucleus was less than 1%, relative to anisole.

EXAMPLE 2

500 parts of a dry, strongly acid cation exchanger (polystyrenesulphonic acid crosslinked with 4% by weight of divinylbenzene) are located in a fixed bed in a vertical tube (internal diameter: 40 mm; capacity: 2 l) and are swollen to constant volume with pyrocatechol. At the bottom end of the reactor, a feed line is provided, through which the reaction solution is metered under a pressure which counter-balances the pressure loss in the column. The top end of the reactor is provided with an outlet through which the reaction mixture can flow out into a receiver.

A solution, warmed to 110° C., of 1,100 parts of pyrocatechol and 79 parts of diethyl ether (molar ratio 10:1) flows through the fixed bed from the bottom upwards. The average residence time of the liquid phase, relative to the empty tube, is 8 hours. A temperature of 120° C. is established inside the reactor by external heating.

After a stationary state has been established, the reaction solution flowing out at the top end of the reactor has the following composition (determined by gas chromatography): 984 parts of pyrocatechol, 152 parts of o-ethoxyphenol (guaethol), 9 parts of water, 36 parts of diethyl ether and 3 parts of unknown compounds which are probably alkylated in the nucleus; that is to say the yield of (guaethol, relative to pyrocatechol reacted, is 97%. The proportion of compounds which are alkylated in the nucleus, relative to guaethol, is below 2% and the proportion of o-diethoxybenzene, relative to guaethol, is below 0.7%.

EXAMPLE 3

A solution, pre-warmed to 60° C., of pyrocatechol in diisopropyl ether (molar ratio: 1:1) is fed into the reactor described in Example 2. The average residence time of the liquid phase in the reactor is 10 hours. A temperaure of 70° C. is established inside the reactor by external heating.

After a stationary state has been established, diisopropyl ether and water are first distilled off from the reaction solution flowing out of the reactor. The reaction mixture which has been freed from these two compounds is analysed by gas chromatography. It has the composition indicated in Table 1, column (a).

The o-isopropoxyphenol is then distilled off from the reaction mixture.

An amount of pyrocatechol equivalent to the amount of o-isopropoxyphenol distilled off is then added to the distillation residue. The mixture is diluted with the same amount by weight of diisopropyl ether and reacted again in the reactor at 70° C. as described above. The reaction solution flowing out is again freed, by distillation, from diisopropyl ether and water and, after its analysis by gas chromatography, from the o-isopropoxyphenol formed and the residue is in turn reacted again, after replenishing the pyrocatechol and diisopropyl ether employed. The operation was repeated a total of 5 times. Table 1 below shows the compositions of the reaction solutions, in each case before separating off the o-isopropoxyphenol, and furthermore the conversion achieved at each passage and the selectivity achieved at each passage.

TABLE 1

| | Composition (%) of the reaction mixtures obtained after distilling off the water of reaction and the diisopropyl ether, after the | | | | | |
|---|---|---|---|---|---|---|
| | (a) 1st passage | (b) 2nd passage | (c) 3rd passage | (d) 4th passage | (e) 5th passage | (f) 6th passage |
| ortho-isopropoxyphenol | 28 | 24 | 24 | 19 | 16 | 16 |
| pyrocatechol | 56 | 45 | 34 | 26 | 27 | 29 |
| unknown components | 16 | 31 | 42 | 55 | 57 | 55 |
| conversion | 37% | 40% | 45% | 50% | 35% | 30% |

TABLE 1-continued

| | Composition (%) of the reaction mixtures obtained after distilling off the water of reaction and the diisopropyl ether, after the | | | | | |
|---|---|---|---|---|---|---|
| | (a) 1st passage | (b) 2nd passage | (c) 3rd passage | (d) 4th passage | (e) 5th passage | (f) 6th passage |
| selectivity | 64% | 54% | 63% | 52% | 76% | 89% |

$$\text{Conversion (\%)} = \frac{\text{pyrocatechol converted (per cycle)}}{\text{pyrocatechol employed (per cycle)}}$$

$$\text{Selectivity (\%)} = \frac{\text{pyrocatechol converted to ortho-isopropoxyphenol (per cycle)}}{\text{total pyrocatechol reacted (per cycle)}}$$

What is claimed is:

1. In the preparation of an alkyl aryl ether by reacting a phenol with an alkylating agent in the presence of a strongly acid cation exchanger, the improvement wherein the alkylating agent consists essentially of a dialkyl ether and the reaction is carried out in liquid phase at a temperature from about 20° to 150° C. with recycle of unreacted starting material.

2. The process according to claim 1, wherein dialkyl ethers of secondary or tertiary aliphatic alcohols are used as the alkylating agent.

3. The process according to claim 1, wherein diisopropyl ether is used as the alkylating agent.

4. The process according to claim 1, wherein for at least about 6 cycles, when the reaction has ended, the alkyl aryl ether and the compounds which have lower boiling points than the latter are distilled off from the reaction mixture and the distillation residue is recycled, the mol ratio of phenol to dialkyl ether being about 1:1.

5. The process according to claim 1, wherein the mol ratio of phenol to ether is about 1:1.

6. The process according to claim 1, wherein the phenol is a polyphenol.

* * * * *